United States Patent
Zuo

(10) Patent No.: US 8,218,954 B2
(45) Date of Patent: Jul. 10, 2012

(54) FRAGRANT ELECTRONIC DEVICE

(75) Inventor: Zhou-Quan Zuo, Shenzhen (CN)

(73) Assignees: Shenzhen Futaihong Precision Industry Co., Ltd., ShenZhen, Guangdong Province (CN); FIH (Hong Kong) Limited, Kowloon (HK)

( * ) Notice: Subject to any disclaimer, the term of this patent is extended or adjusted under 35 U.S.C. 154(b) by 462 days.

(21) Appl. No.: 12/495,881

(22) Filed: Jul. 1, 2009

(65) Prior Publication Data

US 2010/0140371 A1 Jun. 10, 2010

(30) Foreign Application Priority Data

Dec. 4, 2008 (CN) .................... 2008 1 0305959

(51) Int. Cl.
*A01G 13/06* (2006.01)
*A61H 33/12* (2006.01)

(52) U.S. Cl. ........ 392/386; 392/390; 392/403; 392/404; 392/405; 392/406

(58) Field of Classification Search .......... 392/386, 392/390, 403–406
See application file for complete search history.

(56) References Cited

U.S. PATENT DOCUMENTS

| | | | |
|---|---|---|---|
| 3,778,924 A * | 12/1973 | Okui ................ 43/129 |
| 4,588,874 A * | 5/1986 | Napierski .......... 392/390 |
| 4,666,638 A * | 5/1987 | Baker et al. ....... 261/26 |
| 5,126,078 A * | 6/1992 | Steiner et al. ...... 261/26 |
| 5,682,774 A * | 11/1997 | Baumgartner ...... 68/235 R |
| 5,908,140 A * | 6/1999 | Muderlak et al. .. 222/1 |
| 6,378,780 B1 * | 4/2002 | Martens et al. ..... 239/102.2 |
| 6,632,405 B2 * | 10/2003 | Lua ................ 422/124 |
| 7,167,641 B2 * | 1/2007 | Tam et al. ......... 392/405 |
| 7,200,363 B2 * | 4/2007 | Greco et al. ....... 455/66.1 |
| 7,680,691 B2 * | 3/2010 | Kimball et al. ..... 705/22 |
| 8,032,014 B2 * | 10/2011 | Cheung ............ 392/394 |
| 8,068,725 B2 * | 11/2011 | Cheung ............ 392/394 |
| 2002/0043568 A1 * | 4/2002 | Hess et al. ........ 239/69 |
| 2004/0204043 A1 * | 10/2004 | Wang et al. ....... 455/556.1 |
| 2004/0235430 A1 * | 11/2004 | Ma et al. .......... 455/90.1 |
| 2005/0016985 A1 * | 1/2005 | Haas et al. ........ 219/438 |
| 2006/0090290 A1 * | 5/2006 | Lau ................ 15/344 |
| 2010/0001417 A1 * | 1/2010 | D'Amico .......... 261/26 |
| 2010/0185322 A1 * | 7/2010 | Bylsma et al. ..... 700/239 |

* cited by examiner

*Primary Examiner* — Thor Campbell
(74) *Attorney, Agent, or Firm* — Altis Law Group, Inc.

(57) ABSTRACT

A fragrant electronic device includes a main body, a fragrant member and a resilient member received in the main body. The resilient member resists the fragrant member and ensures that the resilient member will not become loose and rattle around in the main body.

16 Claims, 3 Drawing Sheets

FRAGRANT ELECTRONIC DEVICE

BACKGROUND

1. Technical Field

The present disclosure generally relates to an electronic device, and more particularly to a fragrant electronic device.

2. Description of Related Art

Electronic devices, such as mobile phones and PDAs (personal digital assistant), may include a plug-in fragrant member to provide a scent. The electronic device defines a receptacle in which the fragrant member is received. The electronic device further includes a cover covering the receptacle. The fragrant member can volatilize and diffuse a scent. The scent can, for example, make the user feel relaxed and happy.

However, with the continual volatilization, the size of the fragrant member may decrease over time. Then the fragrant member may become loose and rattle around in the receptacle when the user uses the electronic device.

Therefore, there is room for improvement within the art.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout several views, and all the views are schematic.

DETAILED DESCRIPTION

Figure 1:
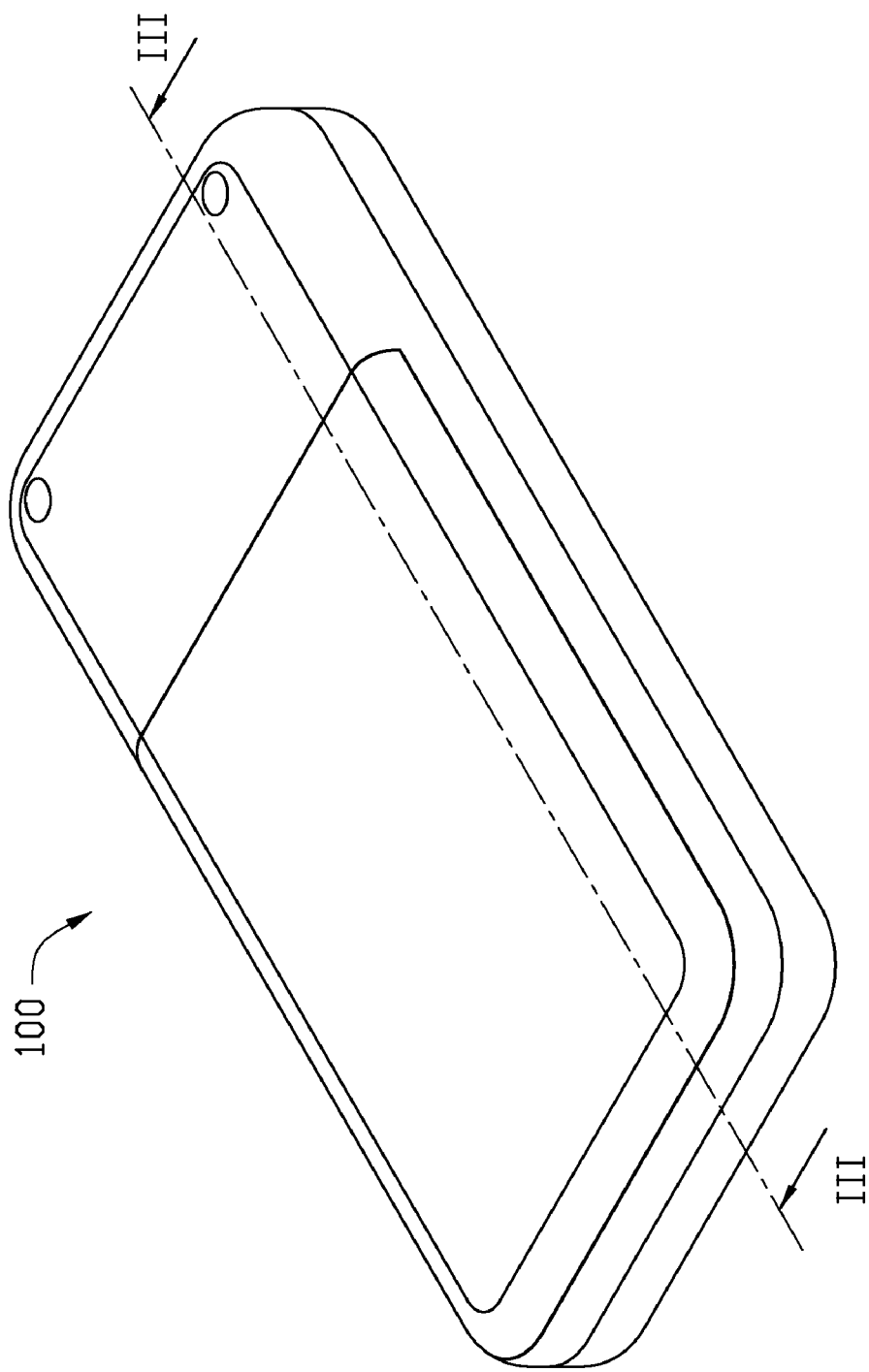
FIG. 1 is an assembled, isometric view of an exemplary embodiment of a fragrant electronic device.
Figure 2:
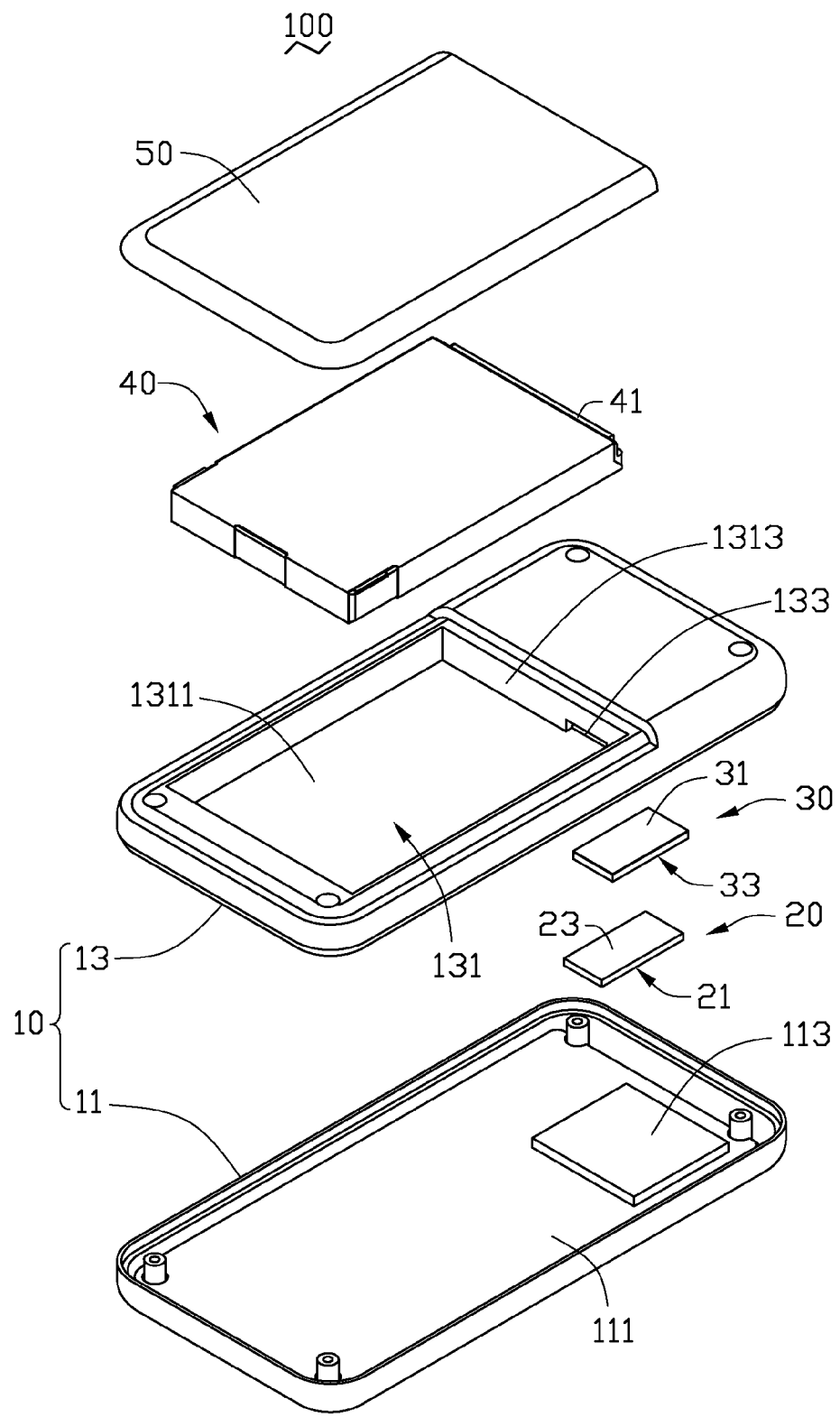
FIG. 2 is an exploded, isometric view of the fragrant electronic device of the FIG. 1.

A fragrant electronic device may be a mobile phone, a PDA, etc. In the illustrated embodiment, the fragrant electronic device is a mobile phone. Referring to FIG. 1 and FIG. 2, the fragrant electronic device 100 includes a main body 10, a fragrant member 20, a resilient member 30, a battery 40, and a battery cover 50 covering the battery 40.

The main body 10 includes a first casing 11 and a second casing 13 coupled to the first casing 11.

The first casing 11 includes a circuit board 111 and a shielding member 113 positioned therein.

The second casing 13 defines a receiving space 131 and a receptacle 133 in which the fragrant member 20 and the resilient member 30 are received. The receiving space 131 is bound by a bottom wall 1311 and a plurality of sidewalls 1313. The receptacle 133 is defined in one of sidewalls 1313 and communicates with the receiving space 131. A first limiting protrusion 1331 is formed in the communicating position of the receptacle 133 and the receiving space 131, extending into the receptacle 133. A second limiting protrusion 1333 is formed at inside of the second casing 13 extending in the same direction as the first limiting protrusion 1331. The first limiting protrusion 1331 and the second limiting protrusion 1333 encircle at least a portion of the receptacle 133 to position the resilient member 30 in the receptacle 133.

The fragrant member 20 has a first resisting surface 21 and a second resisting surface 23 opposite to each other. The receptacle 133 of the main body 10 removably receives the fragrant member 20 through the receiving space 131.

The resilient member 30 provides an elastic force acting on the fragrant member 20. The resilient member 30 may be a compression spring, a spring plate, or a foam member. In the illustrated exemplary embodiment, the resilient member 30 is a foam member. One surface of the resilient member 30 is a connecting surface 31 and another opposite surface is a pressing surface 33. The connecting surface 31 is fixed to the second casing 13 (such as by adhesive or tape), and the pressing surface 33 resists against the fragrant member 20.

The battery 40 may be received in the receiving space 131. The battery 40 has an end surface 41, when the battery is received in the receiving space 131, the end surface 41 resists the sidewall 1313 where the receptacle 133 is defined. The battery cover 50 covers on the battery 40 and ensures that the battery 40 is kept in the receiving space 131.

Figure 3:
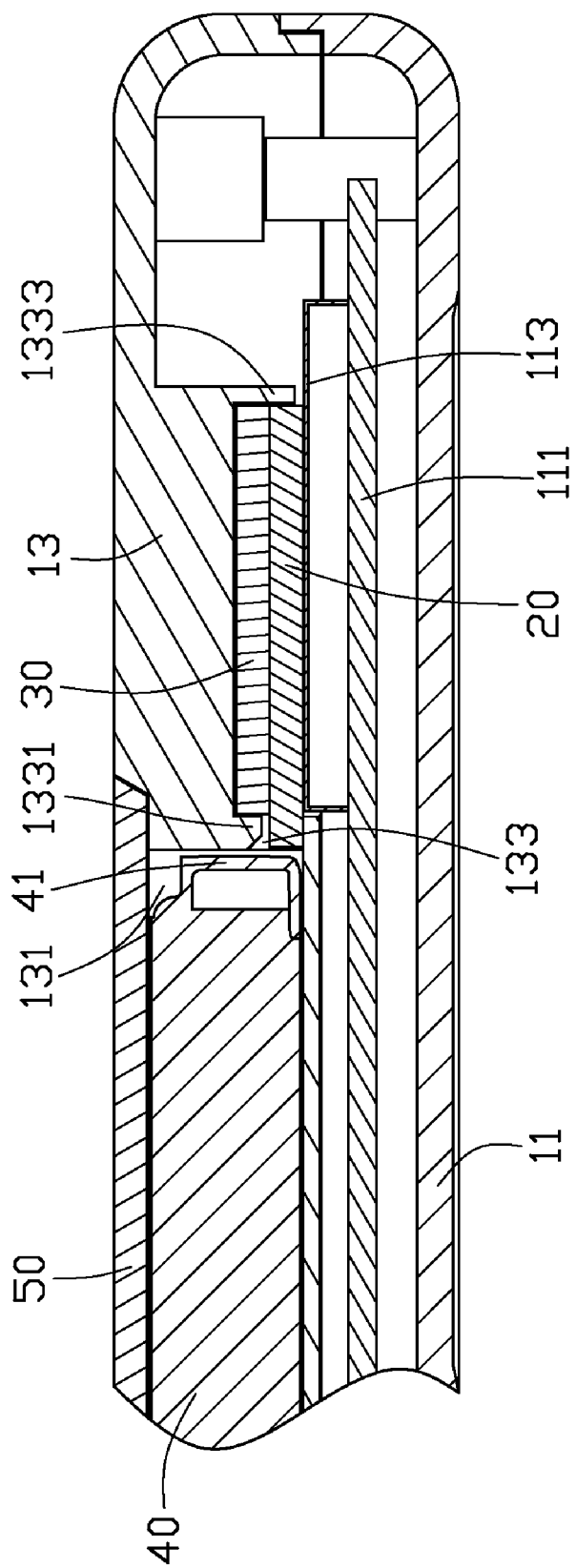
FIG. 3 is a cross-sectional view of FIG. 1, taken along line III-III.

Also referring to FIG. 3, in the fragrant electronic device 100, the second casing 13 is coupled to the first casing 11. The resilient member 30 is received in the receptacle 133 and fixed to the second casing 13. The fragrant member 20 is inserted into the receptacle 133 via the receiving space 131. The first resisting surface 21 resists the shielding member 113 in the first casing 11, and the second resisting surface 23 resists the pressing surface 33 of the resilient member 30. At this state, the pressing force generated between the fragrant member 20 and the resilient member 30 deforms the resilient member 30, such that the fragrant member 20 can be resisted by the resilient member 30.

In use, since the fragrant member 20 is adjacent to the circuit board 17 and the battery 40, when the user uses the fragrant electronic device 100, such as for a telephone call, listening to music or playing games, the circuit board 17 and the battery 40 generate heat, and the heat may accelerate the volatilization of the fragrant member 20. When the fragrant electronic device 100 is used for an extended period of time, more heat may be produced causing a more rapid diffusion producing a stronger scent. Different fragrances may be chosen according to know effects such as inducing relax, alert, or other states in users and installed to the fragrant electronic device 100. When the fragrant electronic device 100 is not in use, the fragrant member 20 may still volatilize according to ambient conditions and diffuse the scent.

Over time, though the thickness of the fragrant member 20 may decrease, the resilient member 30 gradually rebounds and resists the fragrant member 20. Therefore, the fragrant member 20 will not become loose and rattle around in the receptacle 133.

In alternative embodiments, the fragrant member 20 may be positioned elsewhere in the fragrant electronic device 100 such as adjacent to a keyboard, screen, or any other part that will come into close range or contact with the user, thereby, volatilization of the fragrant member 20 can be accelerated by heat from the user or the fragrant electronic device 100, itself.

Finally, while various embodiments have been described and illustrated, the disclosure is not to be construed as being limited thereto. Various modifications can be made to the embodiments by those skilled in the art without departing from the true spirit and scope of the disclosure as defined by the appended claims.

What is claimed is:

1. A fragrant electronic device, comprising:
a main body defining a receptacle;
a fragrant member;
a resilient member;
a circuit board received in the main body;
a shielding member on the circuit board;
wherein when the fragrant member and the resilient member are received in the receptacle, the resilient member is compressed against the fragrant member, and the fragrant member contacts the shielding member and is retained between the shielding member and the resilient member.

2. The fragrant electronic device of claim 1, wherein the main body defines a receiving space to receive a battery, and the receptacle is adjacent and in communication with the receiving space.

3. The fragrant electronic device of claim 2, wherein the fragrant member is removably received in the main body; the fragrant member is moved through the receiving space to be received into or removed from the receptacle.

4. The fragrant electronic device of claim 3, wherein the main body forms a first limiting protrusion and a second limiting protrusion encircling a portion of the receptacle to position the resilient member.

5. The fragrant electronic device of claim 4, wherein the resilient member has two opposite surfaces, one surface is connected on the main body, and the other surface resists against the fragrant member.

6. The fragrant electronic device of claim 4, wherein the main body comprises a first casing and a second casing coupled to the first casing, the receiving space and the receptacle are defined by the first casing, and the circuit board and the shielding member are received in the second casing.

7. The fragrant electronic device of claim 1, wherein the resilient member is a foam member.

8. A fragrant electronic device, comprising:
a main body;
a fragrant member;
a resilient member;
a circuit board received in the main body;
a shielding member on the circuit board;
wherein the fragrant member and the resilient member contacting with each other are received in the main body, and the resilient member provides an elastic force acting on the fragrant member, the fragrant member is retained between the shielding member and the resilient member.

9. The fragrant electronic device of claim 8, wherein the main body defines a receptacle in which the fragrant member and the resilient member are received.

10. The fragrant electronic device of claim 9, wherein the main body further defines a receiving space to receive a battery and communicates with the receptacle, and the receptacle is defined in a sidewall of the receiving space.

11. The fragrant electronic device of claim 10, wherein the fragrant member is removably received in the main body; the fragrant member is moved through the receiving space to be received into or removed from the receptacle.

12. The fragrant electronic device of claim 11, wherein the main body forms a first limiting protrusion and a second limiting protrusion at least partially encircling the receptacle to position the resilient member.

13. The fragrant electronic device of claim 9, wherein the resilient member has two surfaces, one surface is connected to the main body, and the other surface resists against the fragrant member.

14. The fragrant electronic device of claim 8, wherein the fragrant member is adjacent the circuit board.

15. The fragrant electronic device of claim 14, wherein the main body comprises a first casing and the second casing coupled to each other, the receptacle and the receiving space are defined by the first casing, and the circuit board and the shielding member are received in the second casing.

16. The fragrant electronic device of claim 8, wherein the resilient member is a foam member.

* * * * *